(12) United States Patent
Franke et al.

(10) Patent No.: US 11,058,282 B2
(45) Date of Patent: Jul. 13, 2021

(54) COLOUR REFERENCE FOR CALIBRATING A DENTAL COLOUR CAMERA

(71) Applicant: DENTSPLY SIRONA INC., York, PA (US)

(72) Inventors: Frederike Franke, Darmstadt (DE); Marcel Meyer, Bensheim (DE); Teena Steger, Heppenheim (DE)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 16/493,497

(22) PCT Filed: Mar. 16, 2018

(86) PCT No.: PCT/EP2018/056671
§ 371 (c)(1),
(2) Date: Sep. 12, 2019

(87) PCT Pub. No.: WO2018/167274
PCT Pub. Date: Sep. 20, 2018

(65) Prior Publication Data
US 2020/0029792 A1  Jan. 30, 2020

(30) Foreign Application Priority Data
Mar. 17, 2017 (DE) .......................... 102017204463.2

(51) Int. Cl.
*H04N 9/73* (2006.01)
*A61B 1/00* (2006.01)
(Continued)

(52) U.S. Cl.
CPC ............ *A61B 1/00057* (2013.01); *A61B 1/04* (2013.01); *A61B 1/24* (2013.01); *G01J 3/0297* (2013.01);
(Continued)

(58) Field of Classification Search
CPC ...... H04N 9/735; H04N 17/002; H04N 17/02; H04N 1/6033; H04N 1/401; H04N 1/6027;
(Continued)

(56) References Cited

U.S. PATENT DOCUMENTS 8,368,762 B1  2/2013  Chen
2002/0028418 A1* 3/2002 Farag ................... A61C 9/0053
433/29

(Continued)

FOREIGN PATENT DOCUMENTS

DE  02011050564 A1  11/2012
EP  0561228 A2  9/1993
(Continued)

OTHER PUBLICATIONS

Google translation of JP2005/250628A (Year: 2005).*
(Continued)

*Primary Examiner* — Michael Lee
(74) *Attorney, Agent, or Firm* — Dentsply Sirona Inc.

(57) ABSTRACT

The invention relates to a color reference for calibrating a dental color camera comprising a plurality of fields. A surface of the color reference comprises color fields for color calibration as well as white fields and/or gray fields for a white balance and/or a shading correction.

6 Claims, 2 Drawing Sheets

(51) Int. Cl.
*A61B 1/04* (2006.01)
*A61B 1/24* (2006.01)
*G01J 3/02* (2006.01)
*G01J 3/50* (2006.01)
*G01J 3/52* (2006.01)
*H04N 17/00* (2006.01)
*H04N 17/02* (2006.01)

(52) U.S. Cl.
CPC ............... *G01J 3/508* (2013.01); *G01J 3/52* (2013.01); *H04N 9/735* (2013.01); *H04N 17/002* (2013.01); *H04N 17/02* (2013.01)

(58) Field of Classification Search
CPC .... H04N 1/6041; A61B 1/00057; A61B 1/04; A61B 1/24; G01J 3/0297; G01J 3/508; G01J 3/52; G01J 3/524; G01J 3/0202
USPC .......................................................... 348/44
See application file for complete search history.

(56) References Cited

U.S. PATENT DOCUMENTS

| | | | | |
|---|---|---|---|---|
| 2004/0095385 | A1* | 5/2004 | Koo | G06T 15/20 715/757 |
| 2004/0240728 | A1* | 12/2004 | Saikawa | H04N 21/4334 382/162 |
| 2008/0044082 | A1* | 2/2008 | Muller | G01J 3/50 382/162 |
| 2012/0300228 | A1 | 11/2012 | Brothers | |
| 2013/0314559 | A1* | 11/2013 | Kim | H04N 5/23225 348/211.99 |
| 2015/0288952 | A1* | 10/2015 | Popilka | A61B 5/1077 348/46 |
| 2016/0371839 | A1* | 12/2016 | Luo | H04N 9/0451 |

FOREIGN PATENT DOCUMENTS

| | | | |
|---|---|---|---|
| JP | 08152566 | A * | 6/1996 |
| JP | 2005250628 | A * | 9/2005 |
| WO | 2008115547 | A1 | 9/2008 |
| WO | 2012038474 | A1 | 3/2012 |
| WO | 2015082300 | A1 | 6/2015 |

OTHER PUBLICATIONS

International Search Report; PCT/EP2018/056671; Jun. 7, 2018 (completed); dated Jun. 28, 2018.
Written Opinion of the International Searching Authority; PCT/EP2018/056671; Jun. 7, 2018 (completed); dated Jun. 28, 2018.
International Preliminary Report on Patentability; PCT/EP2018/056671; dated Sep. 17, 2019.

* cited by examiner

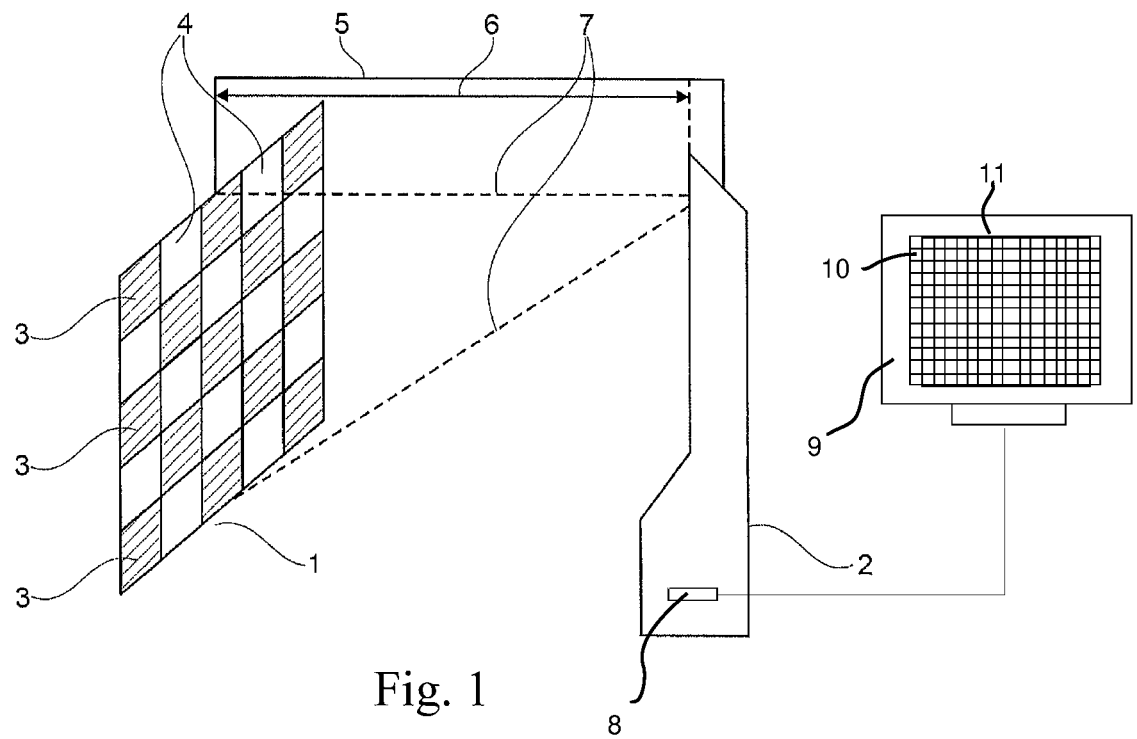
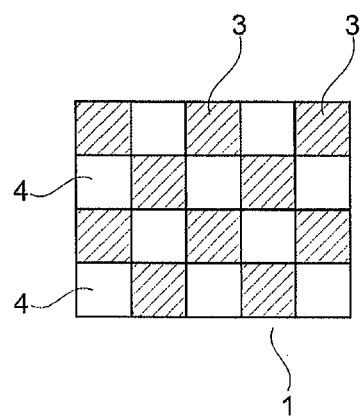
Fig. 2
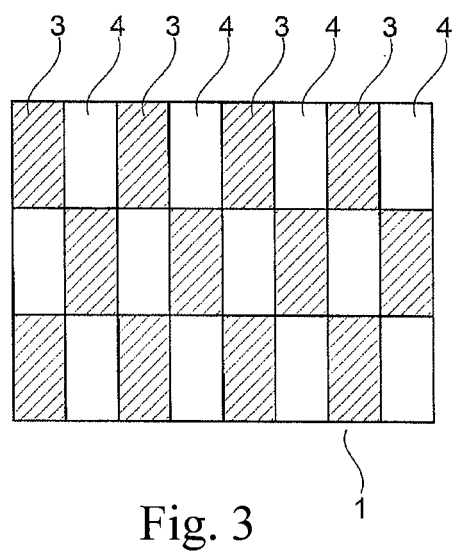
Fig. 3
Fig. 1

COLOUR REFERENCE FOR CALIBRATING A DENTAL COLOUR CAMERA

TECHNICAL FIELD

The invention relates to a color reference and a method for calibrating a dental color camera.

BACKGROUND OF THE INVENTION

A number of color references for calibrating color cameras are known from the state of the art.

In the case of one known color reference, color fields for carrying out a color calibration are arranged on a front side and white and gray fields for carrying out a white balance and a shading correction are arranged on a rear side.

The number of color fields on the front side can be 24, for example, whereby the colors of the color fields can cover a specific spectral range for which the color calibration is to be carried out. The white balance is carried out using the rear side in one step and the color calibration is carried out using the front side in a second step.

WO 2012/038474 A1 discloses a method for determining the color of teeth by means of a color chart positioned on a lip spreader. The color chart can include known color sets of standard colors, such as RGB or CMYK.

US 2012/0300228 A1 discloses a color chart for predicting the print colors of a color printer, wherein the individual color fields are arranged in a grid of squares.

WO 2015/082300 A1 discloses a device for distinguishing the colors of teeth using a smartphone comprising a camera.

Using a spacer, a first polarization filter, a second polarization filter and a color chart are mounted at a fixed distance relative to the camera of the smartphone.

EP 0561228 A2 discloses a method and an arrangement for color image endoscopy with color transformation, whereby the color references are incorporated in the recording of the image. The measured actual color values are then compared with the target color values in order to carry out a color calibration.

One disadvantage of the known color references and methods is that the color calibration and the white balance are carried out in different steps.

It is therefore the object of the present invention to carry out a complete calibration of a color camera comprising a color calibration and a white balance in as simple a manner as possible.

SUMMARY OF THE INVENTION

The invention relates to a color reference for calibrating a dental color camera comprising a plurality of fields. A surface of the color reference comprises color fields for color calibration as well as white fields and/or gray fields for a white balance and/or a shading correction.

The color reference can be a rectangular plate, for example, which has both the color fields and the gray and/or white fields on the same side. Local changes in brightness in the image field, such as vignetting, inhomogeneous illumination or chromatic aberrations, can also be corrected with white balance and a shading correction. Therefore, for a white balance and a shading correction, measured actual values of the brightness and/or hue of the white fields are determined over the entire image field and compared with the target values of said white fields. For example, the decrease of the brightness toward the edge of the image field, so-called vignetting, can be corrected with the white balance and the shading correction.

The shading correction is the equivalent of a local white balance, whereby all the pixels of the optical image are set to the same gray value using calibration data.

Both white fields and darker gray fields can be used to carry out the white balance and the shading correction.

The color fields are used for the color calibration, whereby the colors of the color fields are evenly arranged inside or even slightly outside a color spectrum or color space to be calibrated. Thus, actual values are determined for the brightness and/or the color values for the individual color fields and compared with known target values of said color fields.

Calibration data for all the pixels of the optical image is obtained from the comparison of the actual values with the target values of the white fields.

The calibration data of the white balance and the shading correction can be stored in the form of a transformation matrix, for example.

The calibration data of the individual colors is obtained from the comparison of the actual values with the target values of the color fields.

The calibration data of the color calibration of the individual colors can, for example, also be stored in the form of a lookup table.

The color fields can, for example, include the following colors: yellow, light brown, black, red brown, light gray, light blue, light violet, light orange, dark green, dark violet, dark blue, pink, light green, medium yellow.

The target values for the color values and the brightness values of the color fields and the white fields of the respective color reference are already known before the calibration and can, for example, be stored in a memory.

One advantage of said color reference lies in that the white balance and the shading correction and also the color calibration can be carried out in one step by measuring only one optical image.

The color fields can advantageously comprise at least three different colors.

This makes it possible to carry out a rough color calibration. The number of color fields can also be 24 or more. A higher number of different color fields makes a more accurate color calibration possible.

The white and/or gray fields are evenly distributed on the surface of the color reference.

The even distribution of the white fields makes a white balance and shading correction over the entire image field possible.

The fields can advantageously have a rectangular shape, whereby the color fields and the white or gray fields are alternately arranged relative to one another, in the form of a checkerboard.

As a result of the checkerboard arrangement, the color fields and the white fields are alternately arranged relative to one another in each direction. This permits an even distribution of the white fields over the entire image field.

The fields can advantageously have a square shape.

The square shape of the individual fields makes a compact design of the color reference possible.

The fields can advantageously be immediately adjacent to one another.

A compact design of the color reference is thus made possible. The segmentation of the individual fields is facilitated as well, because there are no intermediate areas.

The color reference can advantageously comprise a holder, whereby the holder can be attached to the color camera in order to arrange the color reference at a defined distance and with a defined orientation relative to the color camera.

The color reference can thus be arranged relative to the color camera by means of the holder in such a way that the image field of the color camera covers the entire color reference.

The invention further relates to a method for calibrating a dental color camera using the color reference. The color reference is recorded by the dental color camera, wherein an optical image is produced, wherein a color value and/or at least one brightness value is determined for at least one pixel of at least four of the recorded white fields and/or gray fields and the white balance and/or the shading correction is carried out, wherein an actual color value is determined for at least three of the recorded color fields and compared with a stored target color value for the respective color field, wherein white balance calibration values are determined for every pixel of the optical image for carrying out the white balance and color calibration values are determined for every color of the color fields.

The color value and/or the brightness value for a pixel can be used in the form of an RGB value, for example.

The white balance and/or shading correction is therefore carried out in the first step using the white fields, whereas the color calibration is carried out in the second step using the color fields.

For the white balance and the shading correction, an actual value of the color value and/or the brightness value is determined from the optical image for at least one recorded pixel of at least four of the recorded white fields and compared with the known target value of the white fields. A calibration value is then determined for at least one pixel of each of the white fields. Calibration values for the remaining pixels can, for example, be determined by interpolation.

The actual value can also be determined for each pixel of the white fields and compared with the target value. The progression of the brightness across the image field, for example, is thus determined with more accuracy.

The actual value can, for example, also be determined for only every fourth pixel of the white fields.

The color calibration is subsequently carried out, whereby an actual value of the color value and/or the brightness value is determined for at least three of the recorded color fields, for example in the form of an RGB value, and compared with the known target value of the respective color field. A color calibration value is then determined for each color of the individual color fields. Color calibration values for the remaining colors of the color space to be calibrated can, for example, be determined by interpolation.

The white balance calibration values and the shading correction calibration values of the individual pixels and the color calibration values of the individual colors can then be stored as calibration data.

One advantage of said method lies in that the white balance, the shading correction and the color calibration can be carried out in one step after an optical image of the color reference has been recorded. The white balance, the shading correction and the color calibration can also be carried out by a computer unit, such as a computer, microcomputer or microchip, without a user interaction.

The individual fields of the recorded optical image can advantageously be segmented using a segmentation algorithm.

The segmentation algorithm identifies the boundaries of the individual fields and partitions them into color fields and white fields. The segmentation algorithm can be carried out fully automatically by means of the computer unit.

The white balance and the shading correction are carried out across the entire surface of an image field of the dental color camera, whereby, based on the color values and/or the brightness values of the white fields or gray fields, an interpolation algorithm is used to determine a white balance and a shading correction over the entire image field, also including regions of the color fields.

The interpolation algorithm makes it possible, for example, to determine the progression of the brightness values across the entire image field. The brightness values of the individual white fields are determined, whereby an interpolation across the color fields between the white fields is carried out. The interpolation algorithm can, for example, fit an appropriate function between the individual brightness values of the white fields. The interpolation algorithm can be carried out fully automatically by means of the computer unit.

The color reference can advantageously comprise a holder, whereby the color reference is arranged at a defined distance and with a defined orientation relative to the color camera by means of the holder prior to recording the optical image in such a way that the depiction of the color reference in the optical image covers the entire image field.

With the holder, the color reference can be arranged at a defined distance with a defined orientation relative to the color camera so that the entire image field is covered and the accuracy of the calibration is improved.

The color reference can advantageously be arranged perpendicular to a recording direction of the color camera by means of the holder.

This facilitates the fully automatic execution of the calibration.

Calibration data can advantageously be obtained for the entire image field after the white balance, the shading correction and the color calibration are carried out.

The calibration data over the entire image field is obtained by comparing the measured actual values of the brightness values and the color values with the known target values. The calibration data can, for example, comprise correction coefficients for the individual pixels of a sensor of the color camera.

The obtained calibration data can advantageously be stored in a memory to be used to correct the optical images of the color camera.

The calibration data are therefore applied to the optical images after the calibration has been carried out, in order to carry out a correction. The calibration data can, for example, be stored in the form of a transformation matrix or a lookup table.

BRIEF DESCRIPTION OF THE DRAWINGS

The invention will be explained with reference to the drawings. The drawings show:

FIG. 1 a color reference in the form of a plate for calibrating a dental color camera, FIG. 2 a color reference having square fields, FIG. 3 a color reference having rectangular fields, FIG. 4 a color reference having diamond-shaped fields.

DETAILED DESCRIPTION OF THE INVENTION

Figure 4:
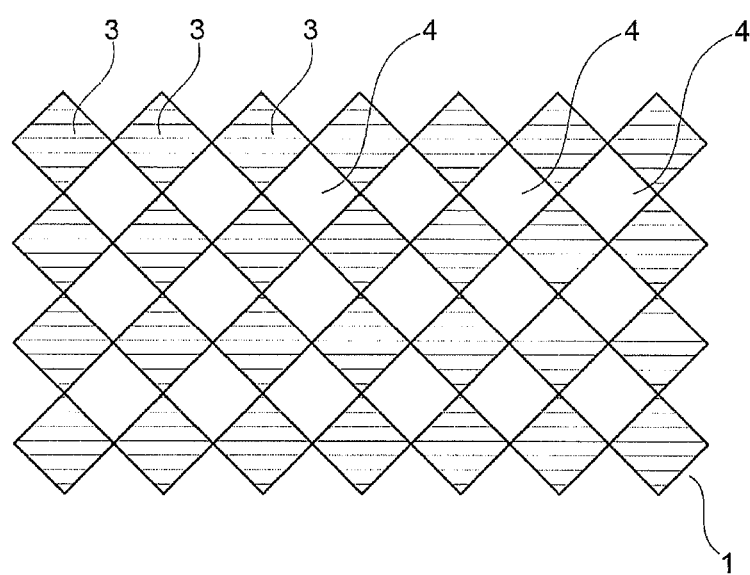

FIG. 1 shows a color reference 1 in the form of a plate for calibrating a dental color camera 2, comprising color fields 3 and white fields 4. In the depicted embodiment, the fields 3 and 4 are square-shaped and are arranged relative to one another in the manner of checkerboard. A holder 5 is disposed on the color reference 1 and can be attached to the color camera 2 in such a way that the color reference 1 can be arranged at a defined distance 6 and with a set orientation relative to the color camera 2. The color reference 1 is arranged in such a way that the fields 3 and 4 of the color reference 1 cover the entire image field 7 of the color camera 2, whereby the boundaries of the image field 7 are indicated by the dashed lines. FIG. 1 also includes the optical image 11, the pixels 10, the sensor 8 and the computing unit 9.

FIG. 2 shows a further embodiment of the color reference 1, wherein the color fields 3 and the white fields 4 are arranged in four lines and five rows in the manner of a checkerboard, wherein the fields 3 and 4 are square-shaped.

FIG. 3 shows a further embodiment of the color reference 1, wherein the color fields 3 and the white fields 4 are shaped like elongated rectangles and are arranged in three lines and eight rows in the manner of a checkerboard.

FIG. 4 shows a further embodiment of the color reference 1, wherein the color fields 3 are shown hatched and the white fields 4 are diamond-shaped and are arranged in the manner of a checkerboard.

REFERENCE SIGNS

1 Color reference
2 Color camera
3 Color fields
4 White fields
5 Holder
6 Distance
7 Image field

The invention claimed is:

1. Method for calibrating a dental color camera using a color reference, wherein the method comprises the steps of:
   recording the color reference by a dental color camera, the color reference including color fields and white and/or gray fields;
   producing an optical image,
   determining a color value and/or at least one brightness value for at least one pixel of at least four recorded white and/or gray fields and comparing the determined color value and/or at least one brightness value to a known target value of the white fields to obtain a first white balance calibration value,
   determining other color values for at least three recorded color fields and comparing the determined other color values to a known target value of the color fields to obtain at least three first color calibration values,
   determining a plurality of other white balance calibration values and/or shading calibration values for a surface of an image field of the dental color camera based on interpolating said determined first white balance calibration value -in order to carry out white balance and/or the shading correction; and,
   determining a plurality of other color calibration values for every color of the color fields based on interpolating said determined at least three first color calibration values for said at least three recorded color fields in order to carry out color correction.

2. Method according to claim 1, wherein each of a plurality fields of the recorded optical image are segmented using a segmentation algorithm.

3. Method according to claim 1, arranging the color reference at a defined distance and with a defined orientation relative to the color camera using a holder prior to recording the optical image such that a depiction of the color reference in the optical image covers the entire image field.

4. Method according to claim 3, wherein the color reference is arranged perpendicularly to a recording direction of the color camera using the holder.

5. Method according to any one of claim 1, wherein calibration data is obtained for the entire image field after the white balance, the shading correction and the color calibration are carried out.

6. Method according to claim 5, wherein the obtained calibration data is stored in a memory to be used to correct the optical images of the color camera.

\* \* \* \* \*